United States Patent [19]

Nelson

[11] 4,273,559
[45] Jun. 16, 1981

[54] ELEMENTAL SUPERSELECTIVE GAS CHROMATOGRAPHIC DETECTION APPARATUS AND METHOD

[75] Inventor: Norvell J. Nelson, Palo Alto, Calif.

[73] Assignee: Varian Associates, Inc., Palo Alto, Calif.

[21] Appl. No.: 972,089

[22] Filed: Dec. 21, 1978

Related U.S. Application Data

[63] Continuation of Ser. No. 822,584, Aug. 8, 1977, abandoned.

[51] Int. Cl.³ .................... G01N 21/72; G01N 27/66
[52] U.S. Cl. .................................. 23/232 E; 422/54; 23/232 C
[58] Field of Search ............ 422/54; 23/232 E, 232 C

[56] References Cited

U.S. PATENT DOCUMENTS

| 3,542,516 | 11/1970 | Clardy | 422/54 |
| 3,585,003 | 6/1971 | Scolnick | 422/54 |
| 3,925,023 | 12/1975 | Kaiser | 422/54 |

Primary Examiner—Michael S. Marcus
Attorney, Agent, or Firm—Stanley Z. Cole; Edward H. Berkowitz

[57] ABSTRACT

An alkali flame ionization detector having an independently biased activator intermediate the flame tip member and the ion collector has been found to yield ion current collector signals which will be selectively positive-going, negative-going or null in response to selected ionic species at an appropriately chosen value of bias potential. Elemental specificity has been found for those values of bias potential which produce a null signal in the presence of a sample.

5 Claims, 10 Drawing Figures

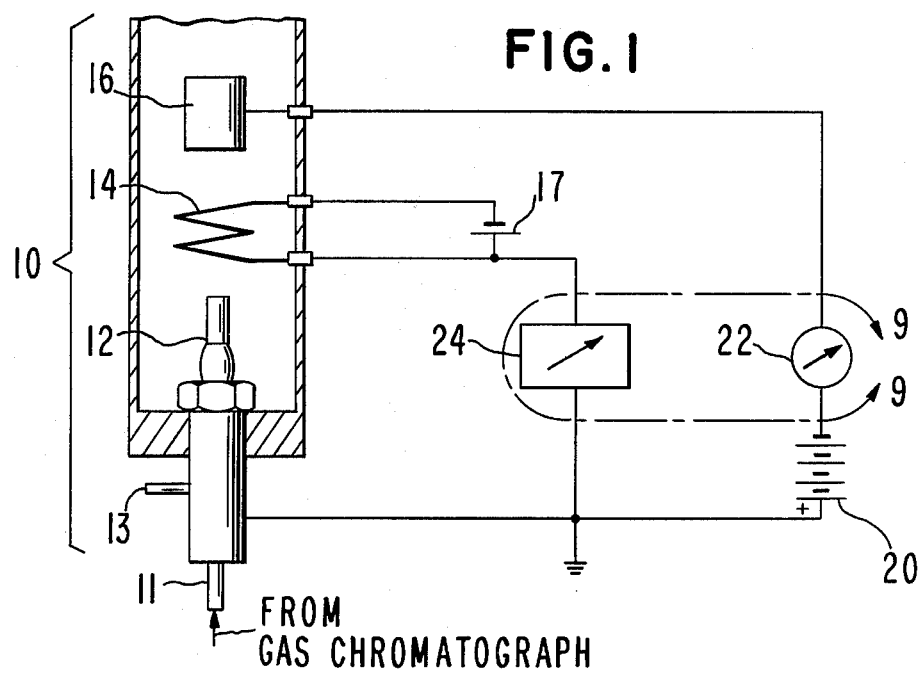
FIG. 1
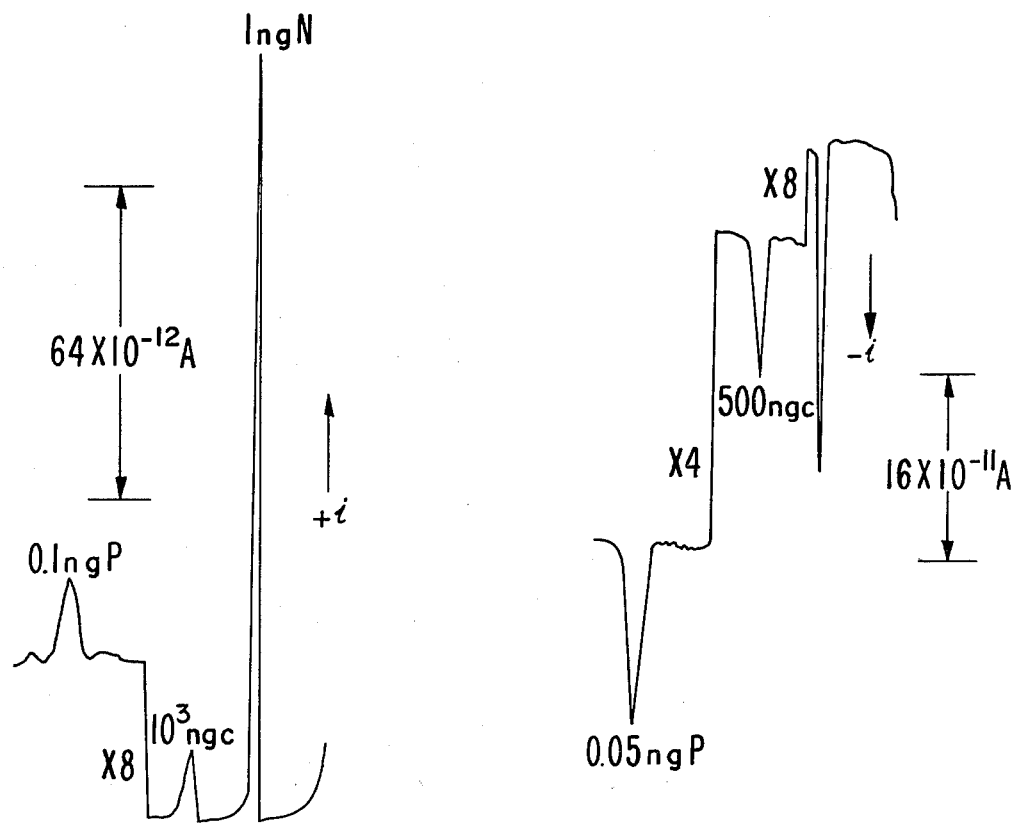
FIG. 2
FIG. 3

- AZOBENZENE (N)
- △ N-METHYLPHENOTHIAZINE (N,S)
- □ TRIBUTYL PHOSPHATE (P)
- ▽ METHYL SULFATE (S)
- + P-IODOANISOLE (I)

ELEMENTAL SUPERSELECTIVE GAS CHROMATOGRAPHIC DETECTION APPARATUS AND METHOD

This is a continuation of application Ser. No. 822,584, filed Aug. 8, 1977, now abandoned.

FIELD OF THE INVENTION

This invention is a development in the field of flame ionization detection useful in elemental analysis apparatus such as gas chromatographic applications and for specific analytic purposes. In particular, a method of analysis has been developed which permits element specific analysis and apparatus compatible with conventional operation.

DESCRIPTION OF THE PRIOR ART

Flame ionization detectors have been extensively developed and are commonly incorporated in gas chromatography apparatus as a detection element for the constituents of gases separated by the process of gas chromatography. One of the most reliable and sensitive detectors for this application is the flame ionization detector. Operationally, the effluent from a gas chromatographic column contains concentrations of vapor and constituents of compounds of interest localized in regions of a carrier gas, usually nitrogen or helium and transported thereby at a steady rate. In the flame detector, hydrogen is added to the gas stream and the mixture is heated or burned in a flame A current produced thereby, either ionic or electronic, is proportional to the amount of material eluted by the column.

In the prior art it has been known to obtain a degree of selective sensitivity, as for example, enhanced sensitivity to halogens or other groups of elements. This selectivity is generally accomplished by passing sample ions through a reaction zone wherein chemical reactions may attenuate the sample ion flux, or alternatively, selectively produce a secondary flux of another ionic species.

Prior art flame ionization detection apparatus also exists which exhibit high sensitivity to and selectivity in response to certain heteroatoms, especially between species containing nitrogen and phosphorous. One such class of detection apparatus is the well-known alkali flame ionization detector, a representative example of which is the Varian Aerograph Alkali Flame Ionization Detector (AFID).

SUMMARY OF THE PRESENT INVENTION

Element specific sensitivity is provided in the present invention by sweeping the bias potential with respect to a flame tip of a reaction zone defined by a heated Rb-coated Pt coil, while continuously monitoring the ion current and normalizing or maintaining a constant flux of vapor sample. The ion current is observed to vary over wide limits of opposite polarity as a function of bias potential and the ion current is extinguished at values of bias potential unique to specific heteroatoms. Thus, ion current null detection may be used to trigger a read-out of bias potential which serves to identify the ionic species. In another mode of operation, an appropriate choice of bias potential permits acquisition of chromatograms having both positive-going and negative-going peaks in response to ionic species having characteristic null potentials greater or less than the chosen bias operating point.

In another mode of operation the AFID of the present invention is cyclically operated with a 100 millisecond period, 97 milliseconds of which operation occur at a constant bias level chosen to optimize the signal to noise ratio in ion current response. A 3 millisecond square pulse is then applied to operate the detector at a bias chosen to optimize the discrimination between e.g. nitrogen and phosphorous, thereby providing a second signal to qualitatively distinguish the unknown by the polarity of the collector signal derived during the 3 millisecond sampling.

Finally, the apparatus is capable of operation as a conventional flame ionization detector (FID) by removal of the potential difference between flame tip member and reaction zone and by operating the reaction zone at ambient temperatures.

OBJECTS OF THE INVENTION

It is an object of the invention to enable improved element specific analysis of gas chromatographic elutant from the current of a flame ionization detector.

It is a feature of this invention to scan the collector current derived from an alkali flame ionization detector by sweeping a bias potential applied to the alkali source of said detector between prescribed limits.

It is another feature of this invention to perform said sweep on a linear time base while maintaining constant the flux of sample introduced to said detector.

It is another feature of this invention to monitor said flux as an alternative to maintaining said flux constant, whereby ion current is normalized to the sample flux quantity.

It is again another feature of this invention to detect a null in ion current intermediate the limits of bias potential and record the value of bias potential associated with said null.

It is again another feature of the invention to operate said detector in an alternative mode whereby said bias potential is selected and maintained constant and chromatographic data comprising both positive-going and negative-going peaks are recorded.

It is yet another feature of the invention to operate the detector cyclically to obtain optimum collector signals during a portion of the cycle at a first selected bias potential and to operate the detector at a second bias potential during the remainder of said cycle whereby operation at the second bias potential furnishes a collector signal which determines the identity of a vapor sample as between a selected pair of distinctive vapors.

BRIEF DESCRIPTION OF DRAWINGS

FIG. 1 is a schematic block diagram of the basic apparatus for practice of the method of the instant invention.

FIG. 2 is a conventional chromatogram of P, C, and N.

FIG. 3 is a negative signal chromatogram corresponding to FIG. 2.

DETAILED DESCRIPTION OF THE PREFERRED EMBODIMENT

Figure 4:
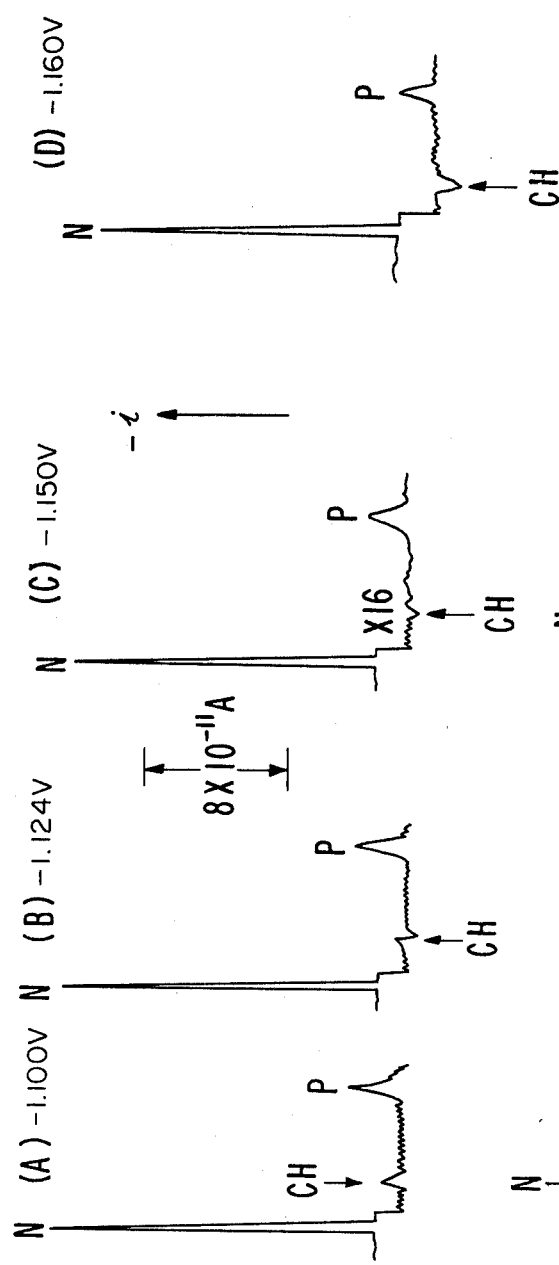
FIGS. 4A–D, inclusive, are chromatograms at successive bias potentials for the alkali source wherein the CH signal traverses a null.

The present invention is best explained with the aid of FIG. 1, a simple idealized system wherein a thermionic detector, or alkali flame ionization (AFID) detector 10 is coupled via sample conduit 11 to the source of effluent, such as a gas chromatograph (GC), not shown. The effluent is introduced to flame tip member 12 whereat a flame is maintained with an oxidant or reductant supplied through annular passage 13. Immediately above the flame space there is located an activator which preferably takes the form of a coil 14 of approximately four turns of platinum ribbon. Typical coils having an inside diameter of 7 mm. and a length of 6 mm. have been successfully employed. A typical dimension for the flame tip member 12 is ⅛ inch and 0.020 inches for the flame orifice in the flame tip member. The coil 14 is liberally covered before use with an oxide or carbonate of an alkali chosen from group IA, or alkaline earth of group IIA containing borate or borosilicate glass. The additive metal oxide (the carbonate is converted to the oxide upon heating) is held onto the Pt coil by containment in either a boron oxide or mixed boron oxide-silicon dioxide matrix. The invention has been successfully practiced using platinum coils coated with a rubidium borate glass, and a rubidium borosilicate glass. The pure borate glasses fuse to a white opaque mass and are apparently quite volatile and water soluble. The rubidium borosilicate glass, however, fuses to a clear deposit and yields better performance. The practice of the present invention is not limited to a particular kind of activator not a specific geometry thereof.

An ion collector 16 is situated to collect positive ions at ground potential when the potential source 20 is adjusted to maintain flame tip member 12 at a positive potential. Coated platinum coil 14 is biased with respect to the ion collector and flame tip member through selectable bias potential source 24. The ion current collected by collector electrode 16 is processed by a sensitive electrometer indicating device 22 which may be a strip chart recorder, for example.

It has been found in the present invention for constant flame tip-collector potential that appropriate variations in the bias potential applied to the platinum coil result in chromatograms which exhibit negative-going peaks in selective response to the elemental composition of the sample. For example, when the platinum coil bias potential is maintained in the range $-6$ to $-90$ volts and the flame jet potential is held within the range $+6$ to $+300$ volts with respect to the collector, only positive-going or "normal" signal responses are observed for CH, N, and P containing species. If, however, the potential of the flame jet is increased to $+480$ volts and the bias potential of the platinum coil is varied, for example, in the region $-3$ to $+5$ volts, the current signals originating from the CH—, N—, and P-containing species can be made positive-going or negative-going in an elementally specific manner. For an appropriate choice of bias potential a null may be obtained in the presence of an otherwise detectable sample concentration. For comparison purposes, a typical normal chromatogram is given in FIG. 2 with the sample concentrations indicated; the N detectability in this case is $8 \times 10^{-14}$ gram atoms per second for the activator and geometry described above. Adjustment of the flame tip potential to $+480$ volts and the platinum coil bias to $+1.002$ volts yields a chromatogram with all negative-going peaks for very similar sample concentrations (FIG. 3). This negative-going chromatogram demonstrates a nitrogen sensitivity of $1.4 \times 10^{-14}$ gram atoms per second, better than 5 times the sensitivity of the positive-going chromatogram.

The versatility of this mode of detection will be illustrated by several examples. Turning now to FIG. 4A-D inclusive, with the flame jet potential held at $+480$ volts, the sense of the CH signal can be changed by varying the platinum coil bias from $-1.100$ volts to $-1.160$ volts as indicated. Each of these chromatograms represent a common sample concentration of 1 ng. N; 10 ngCH; and 0.1 ng P. The chromatogram shown in FIG. 4c exhibits null area for the CH signal notwithstanding the intense CH concentration; the N sensitivity at this point is $-14$ coul per gram atom N, giving a N detectivity of $2.8 \times 10^{-14}$ gram atoms per second. The corresponding P sensitivity is $-7.4$ coul per gram atom P and a P detectivity of approximately $5 \times 10^{-14}$ gram atoms per second. Thus, an effective infinite selectivity over CH is obtained. A simple bias potential adjustment, therefore, allows for discrimination between hetero-atom containing compounds and pure hydrocarbons.

Figure 5:
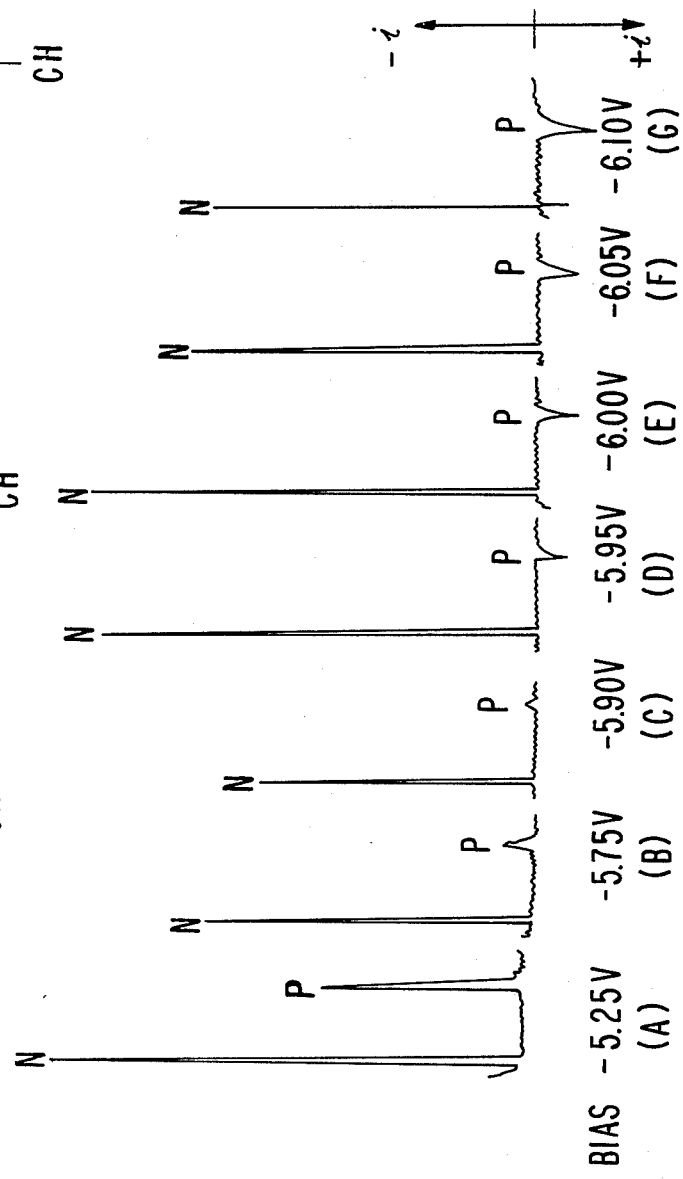
FIGS. 5A–G inclusive are chromatograms at successive bias potentials for the alkali source wherein the phosphorous signal traverses a null.
Figure 6:
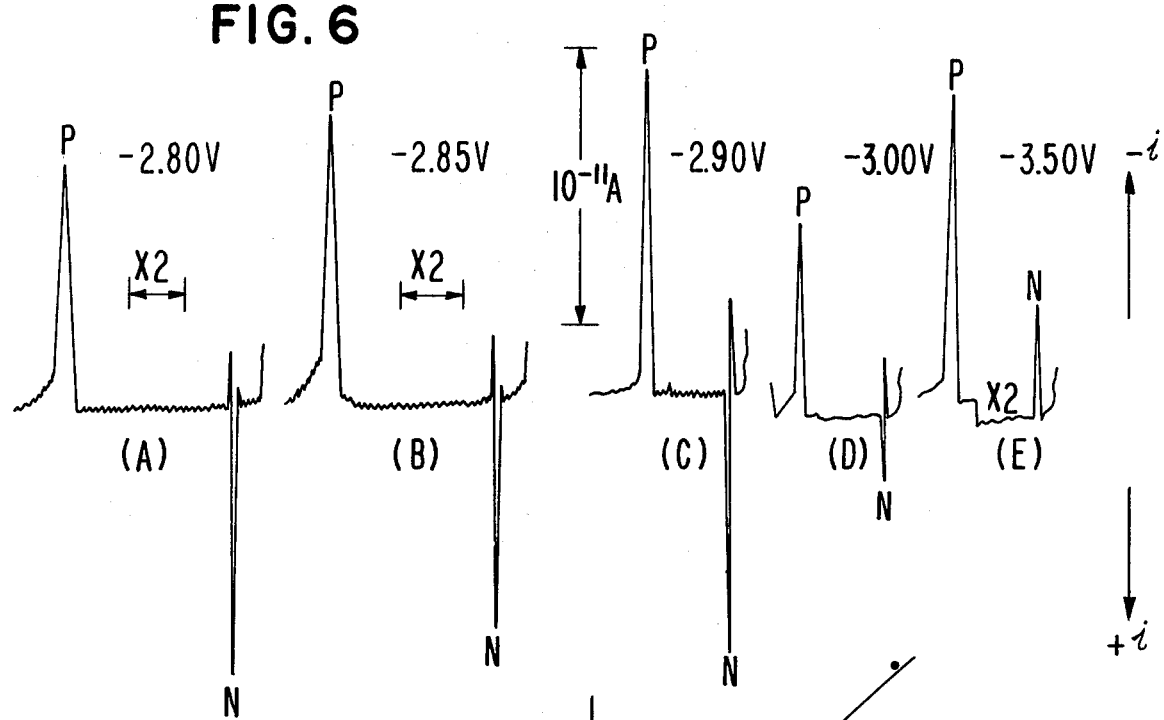
FIGS. 6A–E, inclusive, are chromatograms at successive bias potentials for the alkali source wherein the nitrogen signal traverses a null.

Crossover potentials also exist for the two elements of prime interest, namely N and P. The P crossover is shown in FIG. 5, while that for nitrogen is given in FIG. 6. Again, each spectrum is for a sample of known composition 1 ng. N: 10 ng CH: 0.1 ng P. It is important to note that the crossover potentials for various elemental species are different and well separated (the absolute values of crossover potentials may be dependent upon pressure, activator type, geometry and other factors). Consequently, operation at a bias potential appropriately selected between the respective N and P crossover potentials permits an absolute discrimination between N and P containing compounds. It should also be noted that while these samples also contain 500 ng of $C_{20}H_{42}$ the hydrocarbon is not detectable under the conditions used to obtain these chromatograms. This super selectivity of N relative to P is obtained with some sacrifice in the relative sensitivities of N to P. An example may be seen in FIG. 5a. Here the N sensitivity is about 0.5 coul per gram atom N, giving a N detectivity of about $8 \times 10^{-13}$ gram atoms per second: the corresponding numbers for P are about 3.1 and $1.3 \times 10^{-13}$. The significance of the data lies in the absolute discrimination of N and P.

Figure 7:
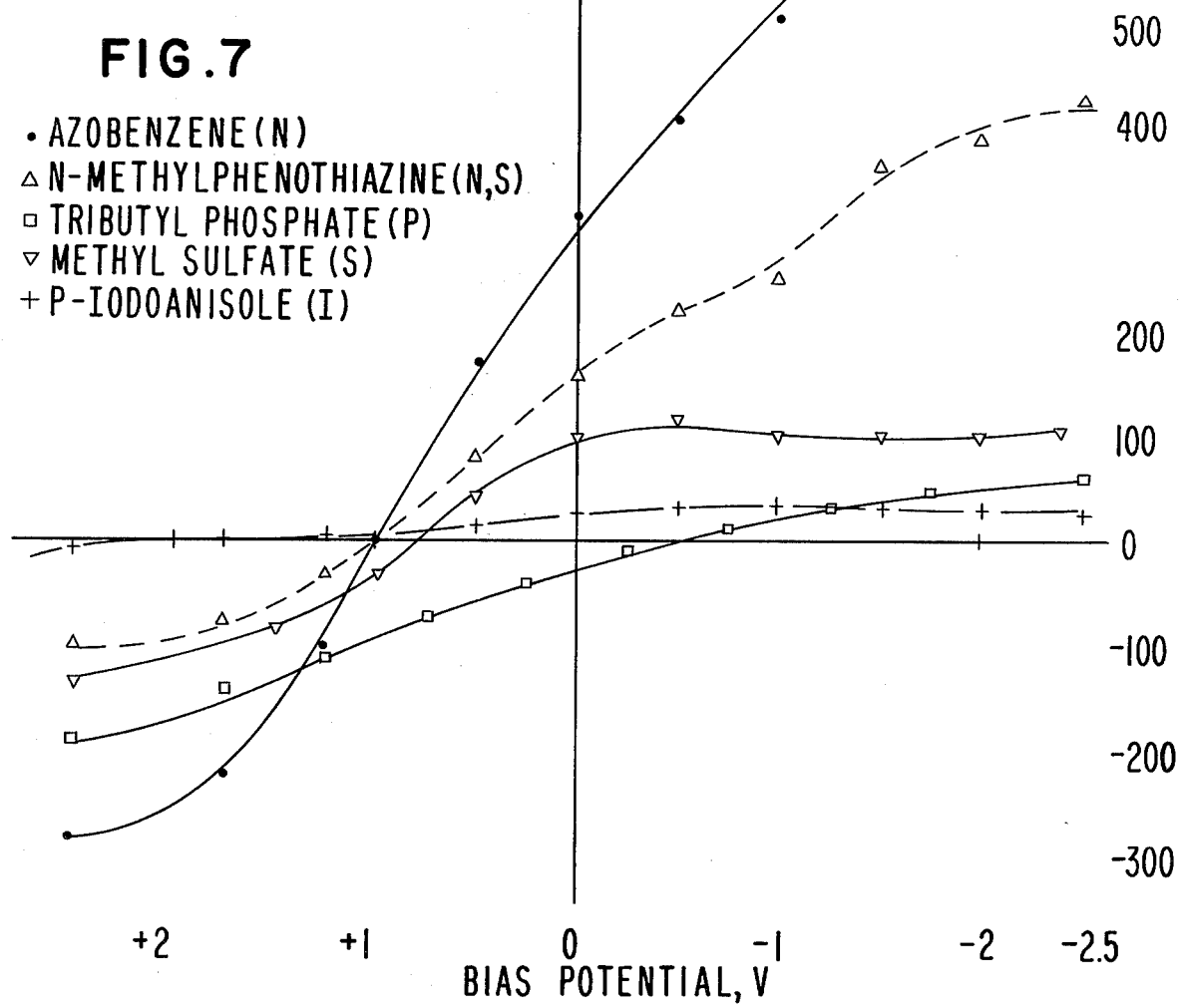
FIG. 7 illustrates the bias dependence of collector current for several different sample gases.

The bipolar spectral response is operationally understood with reference to studies conducted with the above-described apparatus on the observed ion current as a function of bias for a number of sample gases. A representative sample of these observations are shown in FIG. 7. This data was obtained in a straight-forward manner and illustrates that zero-crossing bias values vary widely with the ionic species collected. For given conditions (e.g. activator, geometry, pressure) it is possible to uniquely associate the value of bias which produces a null in ion current with certain elemental constituents of the sample whereby element specific analysis is achievable. By appropriate choice of a constant bias the chromatogram can be made to yield bipolar currents with a predetermined segregation of signals among the two polarities. In another mode of operation, the detection of the ion current crossover, or null point may be employed to identify the ionic species collected.

Figure 8:
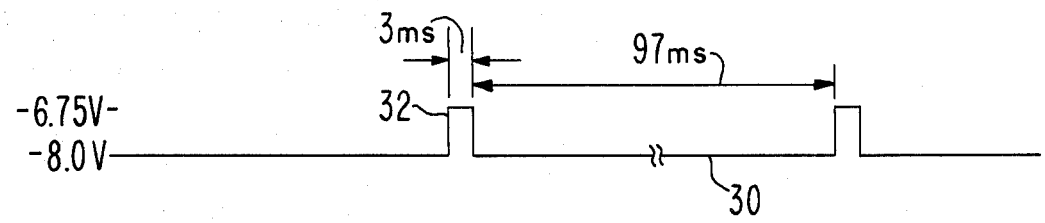
FIG. 8 illustrates a cyclic waveform for alternation between bias potentials.
Figure 9:
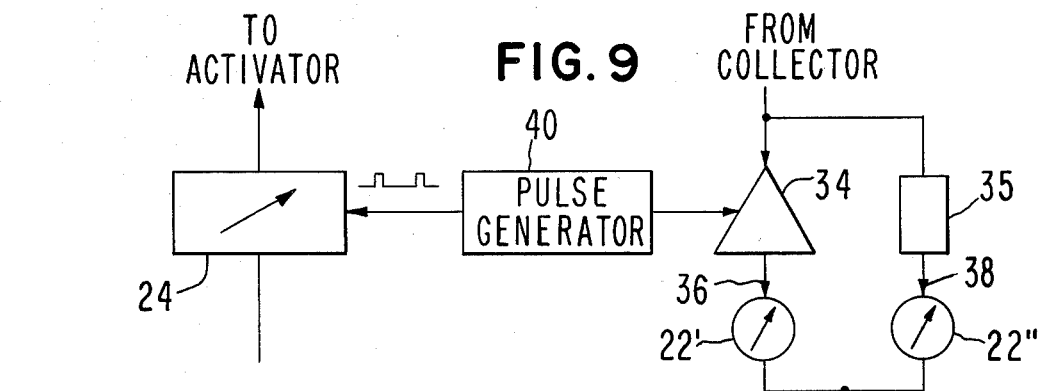
FIG. 9 illustrates an embodiment for cyclic operation yielding both qualitative and quantitative analysis.
Figures 10A, 10B, 10C:
FIG. 10 illustrates the output of a dual channel instrument.
Figures 10A, 10B, 10C:
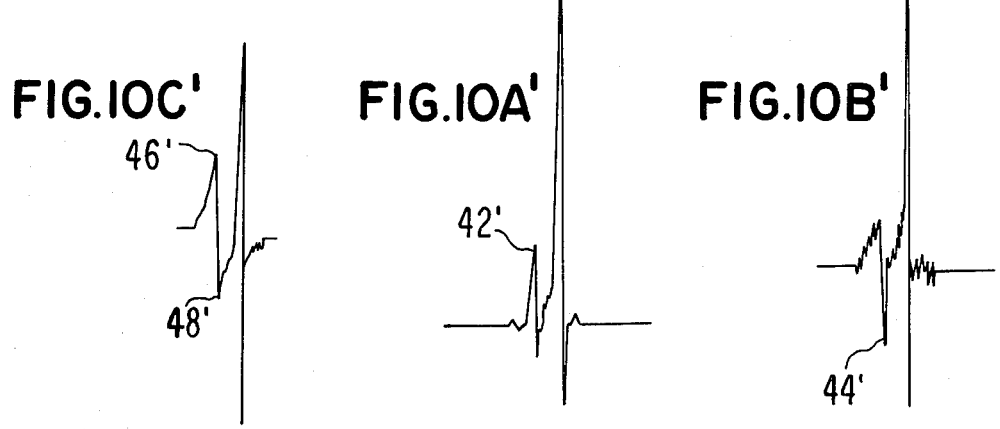

It is apparent that optimum collector signal in the sense of best signal to noise criterion may not coincide with optimum elemental discrimination. In another embodiment of the invention, the bias condition is cyclically altered between two states as indicated in FIG. 8: in the first state the apparatus accumulates data for the preponderant portion 30 of the cycle at a bias level chosen to optimize the signal to noise criterion of collector current. For the remainder of the cycle a square pulse 32, alters the bias condition to a value of bias potential yielding the best discrimination between nitrogen and phosphorous signals. For example, operating at 10 $H_z$, the bias value is set at $-8.0$ volts for a dwell of 97 milliseconds, then switched to $-6.75$ volts for a dwell of 3 milliseconds. This is accomplished schematically by the apparatus of FIG. 9, a modification of FIG. 1. The signals respective of each bias value are segrated by the combination of phase sensitive amplifier 34 which provides a phase synchronized output 36 and filter 35 operating directly upon the collector current to provide output 38 synchronized by square wave generator 40 adapted to cooperate with potential source 24 to apply the bias levels and waveform of FIG. 8 to the activator 14. Filter 35 suppresses the 3 millisecond square pulse from the collector to provide the output 38. The indicating device 22 of FIG. 1 is now replaced by dual channel apparatus 22′ and 22″ by which the respective signals are independently displayed. Representative data obtained by such apparatus are illustrated in FIG. 10 A where peak 42 (100 nanogram sample of azobenzene) is identified by positive going signal 42′ of concurrent recorder trace (FIG. 10 A′) indicating the qualitative identity of corresponding peak 42 as N and in FIG. 10 B the identity of peak 44 (100 nanogram sample of tributyl phosphate) is indicated by negative going signal 44′ of concurrent trace of FIG. 10 B′ as P. In FIG. 10 C equal 100 ng samples of N and P are barely resolved (peaks 46 and 48, but the corresponding identities are established by peaks 46′ and 48′ of the concurrent trace (FIG. 10 C′). More precisely, where the bias is selected for best discrimination between N and P the qualitative data conveyed by a signal such as 42′ is that peak 42 is "not P" and signal 44′ similarly conveys the logical information "not N". The complementation interpretation need not be employed however, where there is a priori knowledge that the unknown peaks can only be N or P.

Since many changes can be made in the above described method and many apparently widely different embodiments of this invention could be made without departing from the scope thereof, it is intended that all matter contained in the above description and shown in the accompanying figures shall be interpreted as illustrative and not in a limiting sense.

What is claimed is:

1. A method of element discrimination comprising:
maintaining a surface defining a boundary of a reaction zone at a first electrical potential relative to a second potential;
supplying a source of alkali metal vapor to said reaction zone;
introducing a sample gas from a flame tip member to said reaction zone, said flame tip member maintained at a reference potential;
introducing another gas to said reaction zone;
inducing selected reactions with said sample gas in said reactions zone;
collecting a plurality of ionic species at a second electrical potential to form a signal proportional to ionic current collected, said ionic species resulting from said reaction;
causing the sense of said ionic current to change for selected components thereof by adjusting of the electric potential distribution between said first potential and said second potential for discrimination between at least two ionic species; and
detecting the value and polarity of the ionic current as a function of the elemental constituents of said sample gas.

2. The method of claim 1 wherein the step of detecting includes identifying the value of said parameter for which the ionic current is substantially zero.

3. The method of claim 1 wherein said adjusted parameter of the electrical potential distribution is the electrical potential of said reaction zone boundary.

4. The method of claim 3 wherein said first potential is adjusted over the range from $-2.5$ volts to $+2.5$ volts with respect to said reference potential and the collector is maintained at substantially 480 volts above said reference.

5. The method of claim 4 wherein said reference potential is ground potential.

* * * * *